(12) United States Patent
Nohara et al.

(10) Patent No.: US 6,648,886 B2
(45) Date of Patent: Nov. 18, 2003

(54) BONESETTING CONNECTING MEMBER

(76) Inventors: Yutaka Nohara, 2-10-A-827, Gamoukotobuki-cho, Koshigaya-shi, Saitama-ken (JP); Kazuya Oribe, c/o Showa Ika Kohgyo Co., Ltd., 3-4-30, Shibakouen, Minato-ku, Tokyo (JP); Hiroshi Takamido, c/o Showa Ika Kohgyo Co., Ltd., 1-1, Hongo, Meito-ku, Nagoya-shi, Aichi-ken (JP)

( * ) Notice: Subject to any disclaimer, the term of this patent is extended or adjusted under 35 U.S.C. 154(b) by 0 days.

(21) Appl. No.: 10/032,534

(22) Filed: Jan. 2, 2002

(65) Prior Publication Data
US 2002/0091388 A1 Jul. 11, 2002

(30) Foreign Application Priority Data
Jan. 10, 2001 (JP) ........................................ 2001-002639

(51) Int. Cl.[7] .................................................. A61F 2/44
(52) U.S. Cl. ............................................................ 606/61
(58) Field of Search ................................. 606/60, 61, 54, 606/62, 69

(56) References Cited

U.S. PATENT DOCUMENTS

| 5,300,073 A | 4/1994 | Ray et al. |
| 5,306,275 A | 4/1994 | Bryan |
| 5,437,669 A | 8/1995 | Yuan et al. |
| 5,498,262 A | 3/1996 | Bryan |
| 5,591,165 A | 1/1997 | Jackson |
| 5,947,965 A | 9/1999 | Bryan |
| 6,015,409 A | 1/2000 | Jackson |
| 6,197,028 B1 | 3/2001 | Ray et al. |
| 6,273,631 B1 * | 8/2001 | Takahashi et al. .......... 403/104 |
| 2002/0032442 A1 * | 3/2002 | Altarac et al. ................. 606/61 |
| 2002/0120272 A1 * | 8/2002 | Yuan et al. .................... 606/61 |

FOREIGN PATENT DOCUMENTS

| WO | 93/14721 | 8/1993 |
| WO | 00/72768 | 12/2000 |

OTHER PUBLICATIONS

Copy of U.S. Patent Application No. 09/956,121.

* cited by examiner

Primary Examiner—Cary E. O'Connor
Assistant Examiner—Candice C. Melson

(57) ABSTRACT

A bonesetting connecting member (1, 17, 19, 21) having an end area supported by a bonesetting tool (5) appropriately mounted to a vertebra (3), thereby connecting the vertebra (3), comprises a polygonal tool engaging portion (11) provided on a body of the bonesetting connecting member (1, 17, 19, 21), and a tool restricting portion (13) for preventing a tool from moving toward opposite sides of the tool engaging portion (11).

8 Claims, 4 Drawing Sheets

FIG.3A
FIG.3B
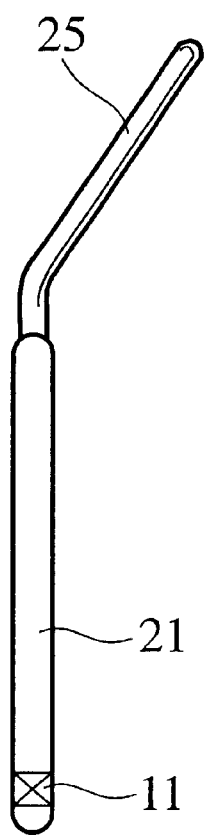
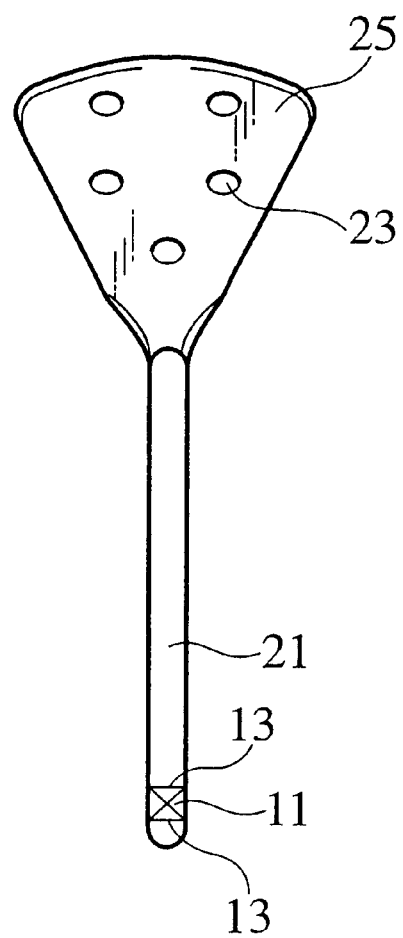

BONESETTING CONNECTING MEMBER

The present disclosure relates to subject matter contained in priority Japanese Patent Application No. 2001-2639, filed on Jan. 10, 2001.

BACKGROUND OF THE INVENTION

1. Field of the Invention

The present invention relates to a bonesetting connecting member such as a rod supported at its end area by a bonesetting tool such as a screw as an implant appropriately mounted to a vertebra. More particularly, the invention relates to a bonesetting connecting member capable of being turned appropriately by a tool, and capable of easily moving in its longitudinal direction by the same tool.

2. Description of the Related Art

In a conventional bonesetting method of a vertebra, implants such as screws as bonesetting tools are threadedly embedded into separated vertebras for example, opposite end areas of a rod member having an appropriate shape as bonesetting connecting member are engaged with rod engaging portions provided on heads of the implants, the opposite end areas are fixed by setscrews, thereby integrally fixing the opposite end areas of the bonesetting connecting member to the bonesetting tool.

When the rod member or the like as the bonesetting connecting member is integrally fixed to the bonesetting tool, in order to combine a curve of the backbone and a curve of the rod member, the rod member is slightly turned around its axis or the rod member is slightly moved in the longitudinal direction in some cases. Some of the conventional rod members are formed with polygonal tool engaging portion on its end so that the rod member can easily be turned around its axis.

In the above structure, a tip end of the polygonal tool engaging portion of the rod member engages a U-shaped tool and turns the same so that the rod member can be turned around its axis. However, when the rod member is moved in its axial direction, the tool comes out from the tool engaging portion. Therefore, the rod member is sandwiched by holding pawls of another tool having engaging pawls which are capable of opening and closing, thereby moving the rod member in the longitudinal direction, or a tool is abutted against an end surface of the rod member.

That is, in the conventional method, when the bonesetting connecting member such as a rod member is slightly turned or slightly moved in the axial direction, there are problems that a plurality of tools are required, management of tools is troublesome, and space for bringing the tool against the end surface of the rod member is required.

SUMMARY OF THE INVENTION

The present invention has been achieved to solve the above-described problems, and the invention provides a bonesetting connecting member having an end area supported by a bonesetting tool appropriately mounted to a vertebra, thereby connecting the vertebra, comprising a polygonal tool engaging portion provided on a body of the bonesetting connecting member, and a tool restricting portion for preventing a tool from moving toward opposite sides of the tool engaging portion.

BRIEF DESCRIPTION OF THE DRAWINGS

FIG. 3A is a side view of a third example of the bonesetting connecting member;

FIG. 3B is a front view of the third example of the bonesetting connecting member.

DETAILED DESCRIPTION OF THE PREFERRED INVENTION

Figure 1:
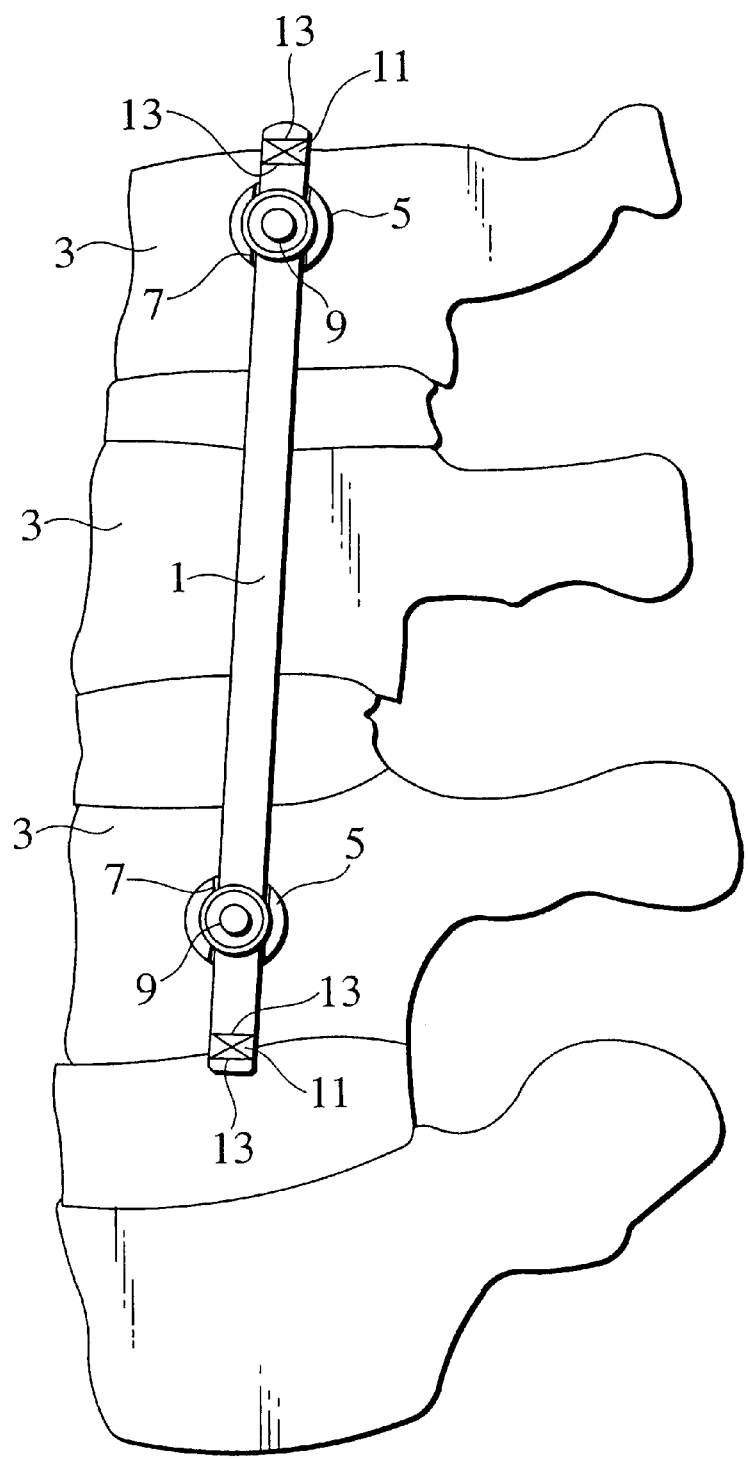
FIG. 1 is an explanatory view showing a first example of a mounting state of a bonesetting connecting member to a vertebra.

As shown in FIG. 1, a bonesetting connecting member according to a first example of the present invention is indicated with a straight rod member 1. Opposite end areas of the rod member 1 are engaged with engaging grooves 7 formed in heads of a pair of screws (implants) 5 as one example of a bonesetting tool threadedly embedded in a vertebral body (vertebra) 3. Each of the engaging grooves 7 is formed in the head in a direction intersecting with an axis thereof. The opposite end areas are integrally fixed to the screws 5 by means of setscrew 9 threadedly engaged with the head.

Figure 4:
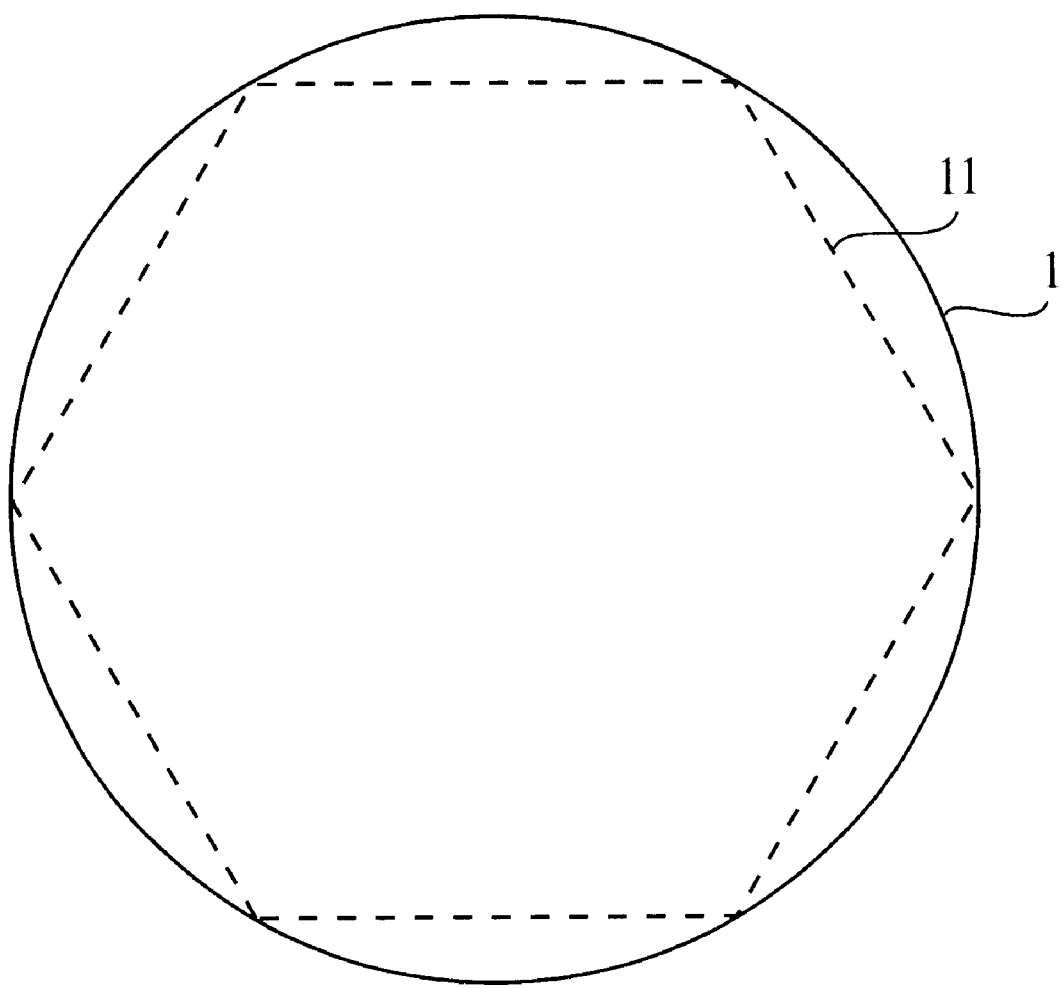
FIG. 4 is an end view of the bonesetting connecting member shown in FIG. 1.

The opposite end areas of the rod member 1 as the bone setting connecting member are formed with polygonal tool engaging portions 11. The tool engaging portion 11 is of polygonal shape having, e.g., regular hexagonal cross section. A diameter of a circle which is inscribed on the polygonal portion is substantially equal to a diameter of the rod member 1, as shown in FIG. 4. Therefore, a step is generated between a plane of the tool engaging portion 11 and an outer peripheral surface of the rod member 1, and this step restricts the movement of the tool in an axial direction of the rod member 1. Thus, opposite sides of the tool engaging portion 11 are formed with steps as tool restricting portions 13 for preventing the tool from moving in the axial direction.

With the above structure, the opposite end areas of the rod member 1 as the bonesetting connecting member are engaged with the engaging grooves 7 formed in the heads of the screws 5 as one example of the bonesetting tool. Prior to integrally fixing by the setscrew 9, a tool (not shown) having a U-shaped tip end is engaged with the tool engaging portion 11 of the rod member 1, and by turning the tool, the rod member 1 can be slightly turned around the axis of the rod member 1.

Therefore, when the rod member 1 is previously curved appropriately in correspondence with a curve of a backbone for example, the curve of the rod member 1 can be adjusted in the curving direction so the curve of the rod member 1 corresponds to the curve of the backbone. In a state in which the tool is engaged with the tool engaging portion 11, if an attempt is made to move the tool in the longitudinal direction of the rod member 1, the tool restricting portions 13 formed on the opposite sides of the tool engaging portion 11 restrict the movement of the tool. Therefore, the rod member 1 is moved in a desired direction in the longitudinal direction, and a position of the rod member 1 with respect to the screw 5 can easily be adjusted.

As understood already, according to this embodiment, by engaging the tool with the polygonal tool engaging portion 11, the rod member 1 as the bonesetting connecting member can be turned around its axis and in this state, the movement in the axial direction can be adjusted by the same tool, and rotation and a position in the longitudinal direction of the bonesetting connecting member can easily be adjusted.

Although the tool engaging portions 11 are provided on the opposite ends of the rod member 1 in the above explanation, the tool engaging portion 11 may be provided only one end, or one or a plurality of tool engaging portions 11 may be provided on a central portion of the rod member 1.

Figure 2A:
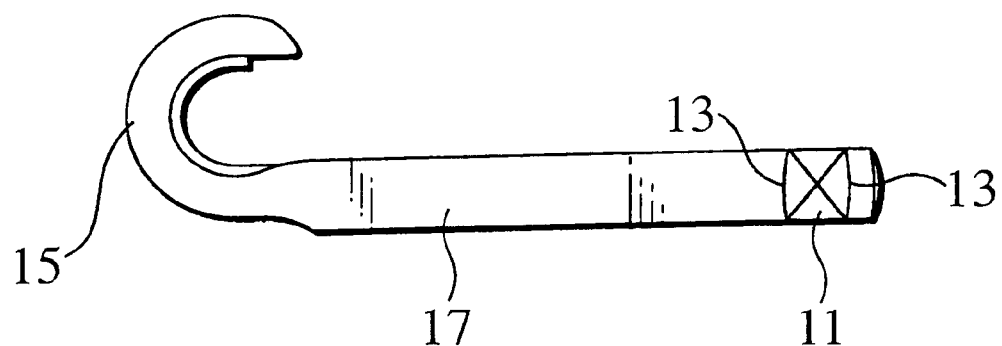
FIG. 2A is an explanatory view showing one mode of a second example of the bonesetting connecting member.
Figure 2B:
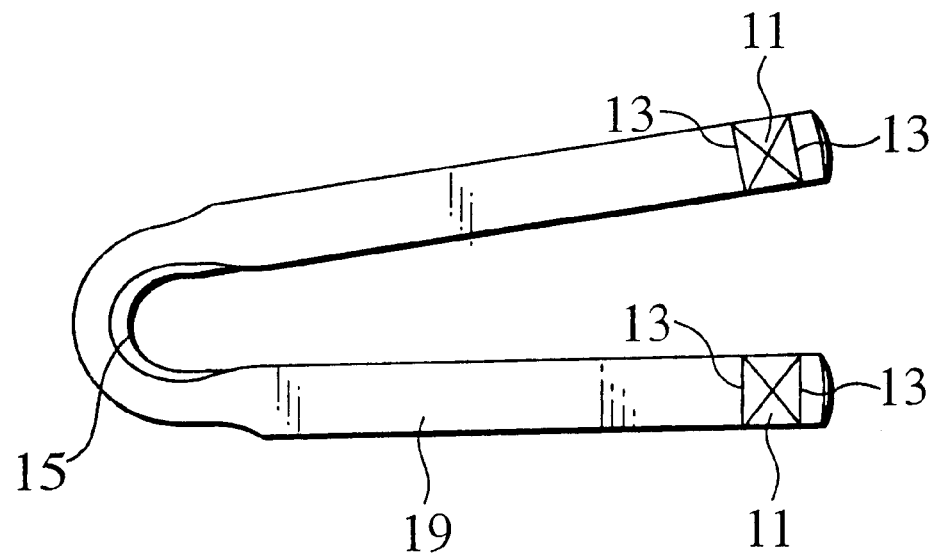
FIG. 2B is an explanatory view showing another mode of the second example of the bonesetting connecting member.

The bonesetting connecting member is not limited to the straight or slightly curved rod member 1 only, and the bonesetting connecting member may be a substantially J-shaped rod member 17 provided at its one end with a spur (not shown) of a vertebral body 3 or a hook 15 retained with a vertebral arch as shown in FIG. 2A for example, or a polygonal tool engaging portion 11 may be formed at an end area or an appropriate position of a substantially V-shaped or J-shaped rod member 19, and the same effect can be obtained.

Further, as shown in FIGS. 3A and 3B, a mounting portion to a cervical vertebra may be formed as a rod 21. The rod 21 of the bonesetting connecting member is formed with a flat portion 25 as a mounting portion to the braincase. A plurality of mounting holes 23 are formed in the flat portion 25. A polygonal tool engaging portion 11 may be formed on the rod 21.

The rod member as the bonesetting connecting member need not be, as shown in FIG. 1, straight in shape nor need not be turned around its axis, but if it is necessary to move the rod member in the axial direction, a groove or a flange-like projection may be formed on an end area of the rod member, a tool may be engaged with the groove or the projection may be brought into abutment against the tool, and by pressing the tool in the axial direction, the rod member may be moved and adjusted in the axial direction.

In this case, the tool for moving and adjusting the rod member in the axial direction is not limited to a special design only if the tool can be engaged with the groove or the projection. Because a holding pawl or the like that can open and close for holding the rod member is not required, a structure of the tool can further be simplified.

What is claimed is:

1. A bonesetting connecting member having an end area supported by a bonesetting tool appropriately mounted to a vertebra, thereby connecting the vertebra, comprising a polygonal tool engaging portion provided on a body of the bonesetting connecting member, and a tool restricting portion for preventing a tool from moving toward opposite sides of the tool engaging portion.

2. A bonesetting connecting member according to claim 1, wherein said tool restricting portion is provided with a plane of said tool engaging portion and an outer peripheral surface of said bonesetting connecting member.

3. A bonesetting connecting member according to claim 1, wherein said bonesetting connecting member is a J-shaped member provided at its one end with a hook.

4. A bonesetting connecting member according to claim 1, wherein said bonesetting connecting member is a V-shaped member comprising a pair of rod members.

5. A bonesetting connecting member according to claim 1, wherein a cross section of said tool engaging portion is regular hexagon in shape.

6. A bonesetting connecting member according to claim 1, wherein further comprising
   a flat portion provided at its one end with a plurality of mounting holes, and
   a rod connected to said flat portion, wherein
   said rod is formed with said tool engaging portion, and said tool engaging portion is provided at its opposite sides with said tool restricting portions.

7. A bonesetting connecting member according to claim 5, wherein a diameter of a circle connected with a polygonal portion provided on said tool engaging portion is substantially equal to a diameter of said bonesetting connecting member.

8. A bonesetting apparatus comprising a pair of implants threadedly embedded in a vertebral body, rods engaging with said implants, and screws for fixing said implants and said rods, wherein each of said rods is formed with a polygonal tool engaging portion, and said tool engaging portion is provided at its opposite sides with tool restricting portions for preventing the tool from moving.

* * * * *

UNITED STATES PATENT AND TRADEMARK OFFICE
CERTIFICATE OF CORRECTION

PATENT NO. : 6,648,886 B2
DATED : November 18, 2003
INVENTOR(S) : Y. Nohara et al.

It is certified that error appears in the above-identified patent and that said Letters Patent is hereby corrected as shown below:

<u>Title page,</u>
Insert Item:
-- [73] Assignee: Showa Ika Kohgyo Co., Ltd., Tokyo, Japan --.

Signed and Sealed this

Thirteenth Day of July, 2004

JON W. DUDAS
*Acting Director of the United States Patent and Trademark Office*